United States Patent
Yoo

(10) Patent No.: US 10,549,008 B2
(45) Date of Patent: Feb. 4, 2020

(54) METHOD FOR PREPARING WOUND DRESSING MATERIAL USING BIOPOLYMER AND WOUND DRESSING MATERIAL USING BIOPOLYMER PREPARED THEREBY

(71) Applicant: MEDITIP CO., LTD., Seoul (KR)

(72) Inventor: Jeoung Hee Yoo, Seoul (KR)

(73) Assignee: MEDITIP Co., Ltd., Seoul (KR)

( * ) Notice: Subject to any disclaimer, the term of this patent is extended or adjusted under 35 U.S.C. 154(b) by 243 days.

(21) Appl. No.: 15/033,187

(22) PCT Filed: Jan. 22, 2016

(86) PCT No.: PCT/KR2016/000693
§ 371 (c)(1),
(2) Date: Apr. 29, 2016

(87) PCT Pub. No.: WO2016/122164
PCT Pub. Date: Aug. 4, 2016

(65) Prior Publication Data
US 2016/0354508 A1 Dec. 8, 2016

(30) Foreign Application Priority Data

Jan. 30, 2015 (KR) .......... 10-2015-0015042
Jan. 20, 2016 (KR) .......... 10-2016-0006839

(51) Int. Cl.
| | | |
|---|---|---|
| A61L 15/28 | (2006.01) | |
| A61L 15/44 | (2006.01) | |
| A61K 31/7036 | (2006.01) | |
| A61L 15/46 | (2006.01) | |
| A61K 31/728 | (2006.01) | |
| A61K 45/06 | (2006.01) | |
| A61L 31/16 | (2006.01) | |
| A61L 31/04 | (2006.01) | |

(52) U.S. Cl.
CPC .......... *A61L 15/44* (2013.01); *A61K 31/7036* (2013.01); *A61K 31/728* (2013.01); *A61K 45/06* (2013.01); *A61L 15/28* (2013.01); *A61L 15/46* (2013.01); *A61L 31/042* (2013.01); *A61L 31/16* (2013.01); *A61L 2300/406* (2013.01)

(58) Field of Classification Search
CPC .............. A61K 31/728; A61K 31/7036; A61K 2300/00; A61K 45/06; A61L 14/44; A61L 15/28; A61L 2100/406; A61L 31/042; A61L 31/16; A61L 15/46; C08L 5/08
USPC .......................................................... 514/40
See application file for complete search history.

(56) References Cited

U.S. PATENT DOCUMENTS

| | | | |
|---|---|---|---|
| 6,180,601 B1 | 1/2001 | Jederstrom | |
| 2002/0098244 A1* | 7/2002 | Miyata | ............... A61L 15/28 424/548 |

FOREIGN PATENT DOCUMENTS

| | | | | |
|---|---|---|---|---|
| CN | 10221085 | * | 8/2013 | ............. A61L 15/28 |
| JP | 2011-0921699 A | | 5/2011 | |
| KR | 10-1015734 B1 | | 11/2008 | |
| KR | 10-2014-0140212 A | | 12/2014 | |
| KR | 10-1841469 B1 | | 3/2018 | |

OTHER PUBLICATIONS

Lee et al, Artificial Organs, 2002, 26(7), 636-646.*
Gupta S et al., entitled "A combined effect of freeze-thaw cycles and polymer concentration on the structure and mechanical properties of transparent PVA gels," Biomed. Mater. 7 (2012) 015006, 9 pages.

* cited by examiner

*Primary Examiner* — Ganapathy Krishnan
(74) *Attorney, Agent, or Firm* — Amster, Rothstein & Ebenstein LLP

(57) ABSTRACT

Disclosed is a method for preparing a wound dressing material using a biopolymer, wherein the wound dressing material prepared by the method can have excellent effects of inhibiting wound infections and preventing adhesions.

2 Claims, 6 Drawing Sheets

[Fig. 1]
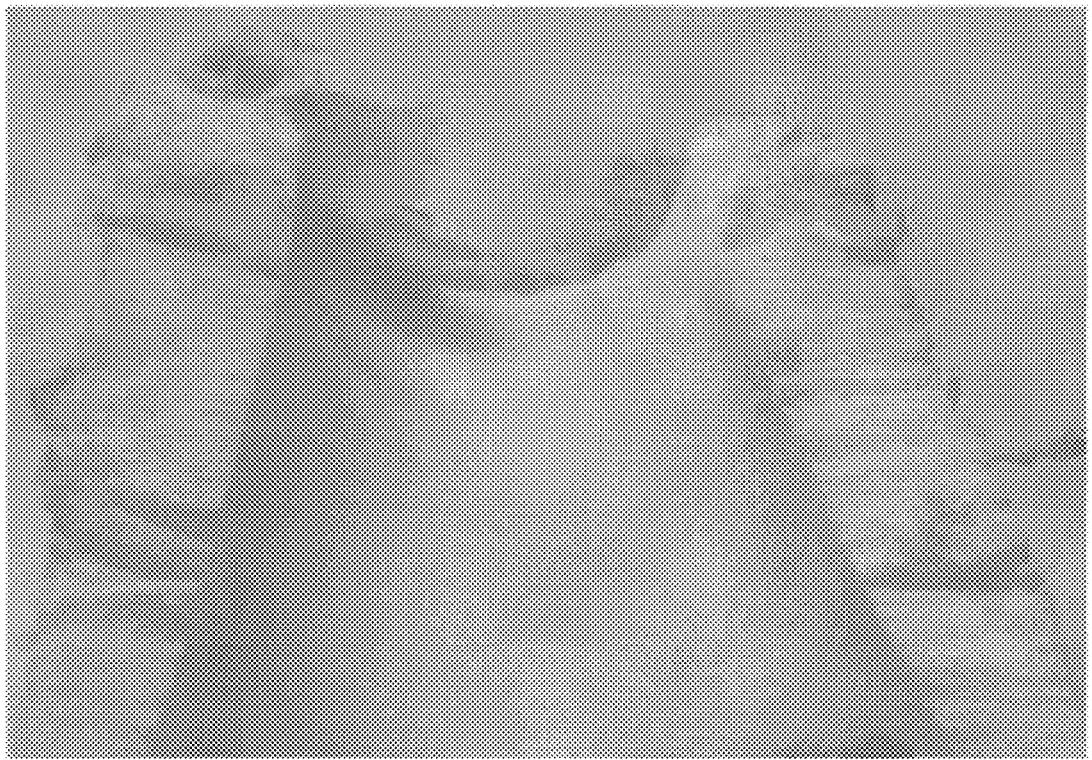
[Fig. 2]

[Fig. 3]
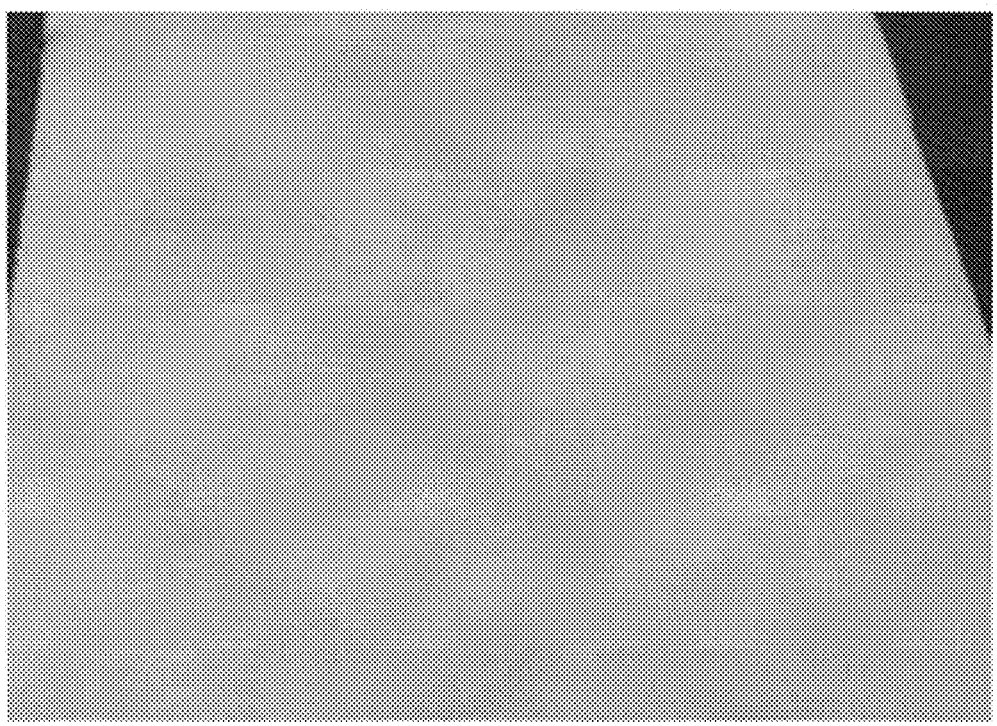
[Fig. 4]
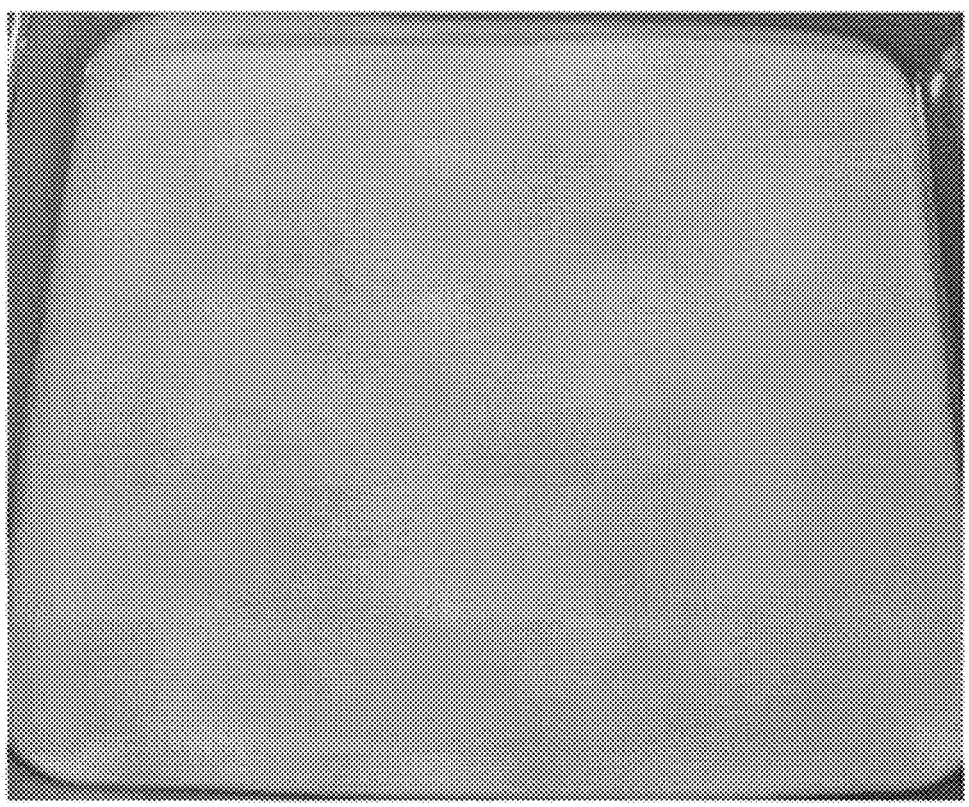

[Fig. 5]
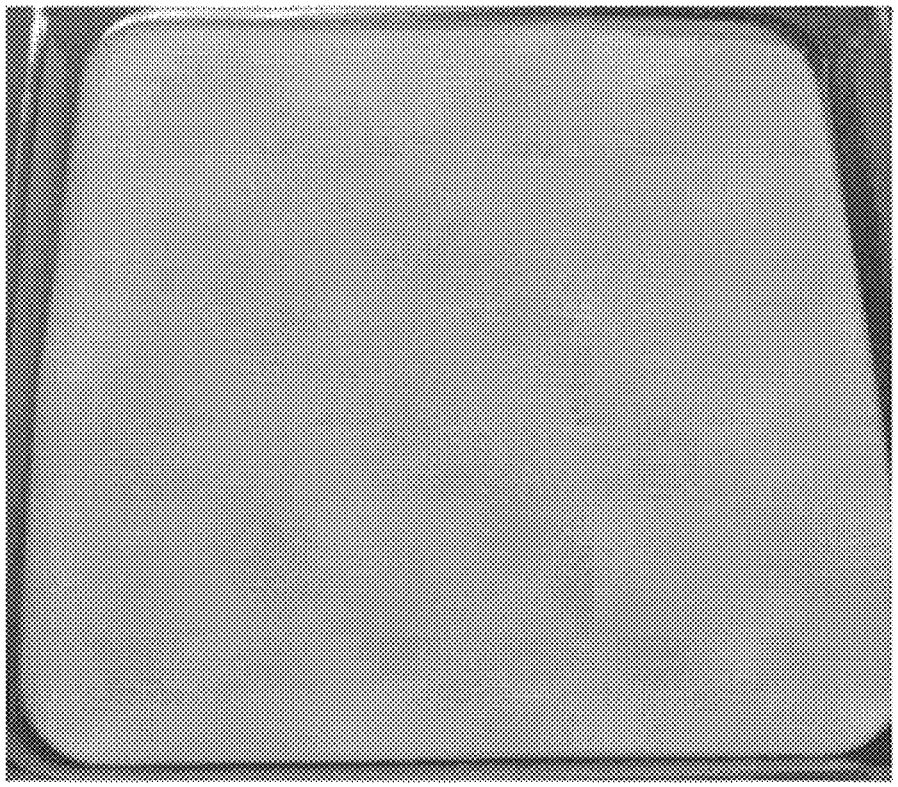
[Fig. 6]

[Fig. 7]
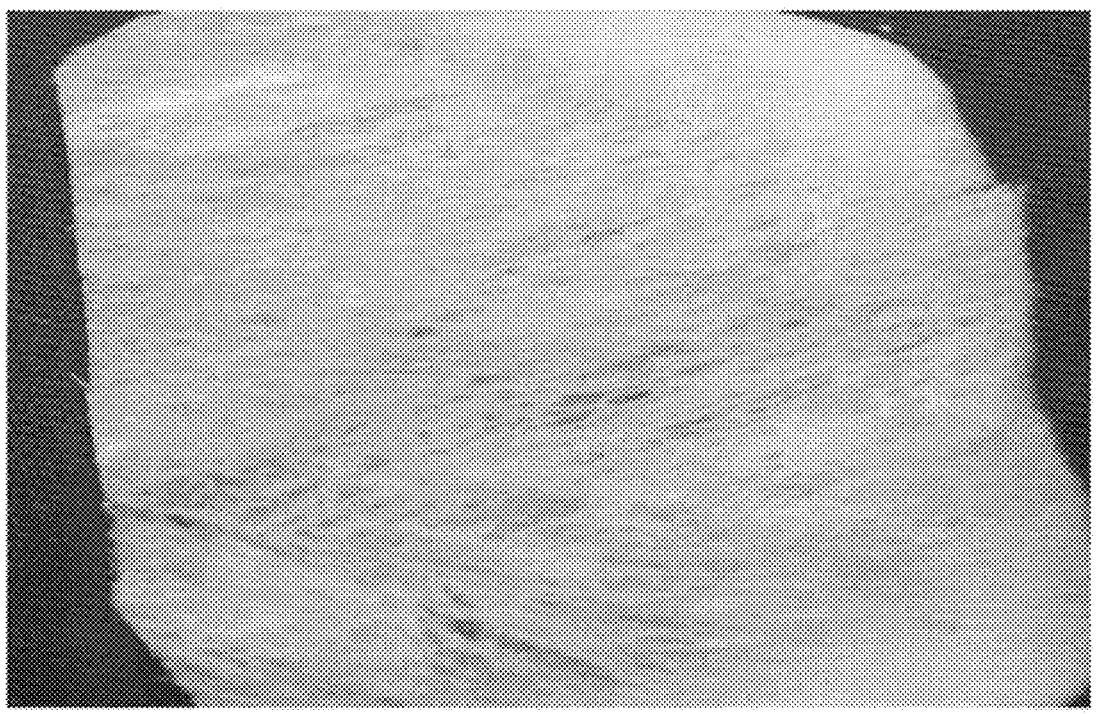
[Fig. 8]
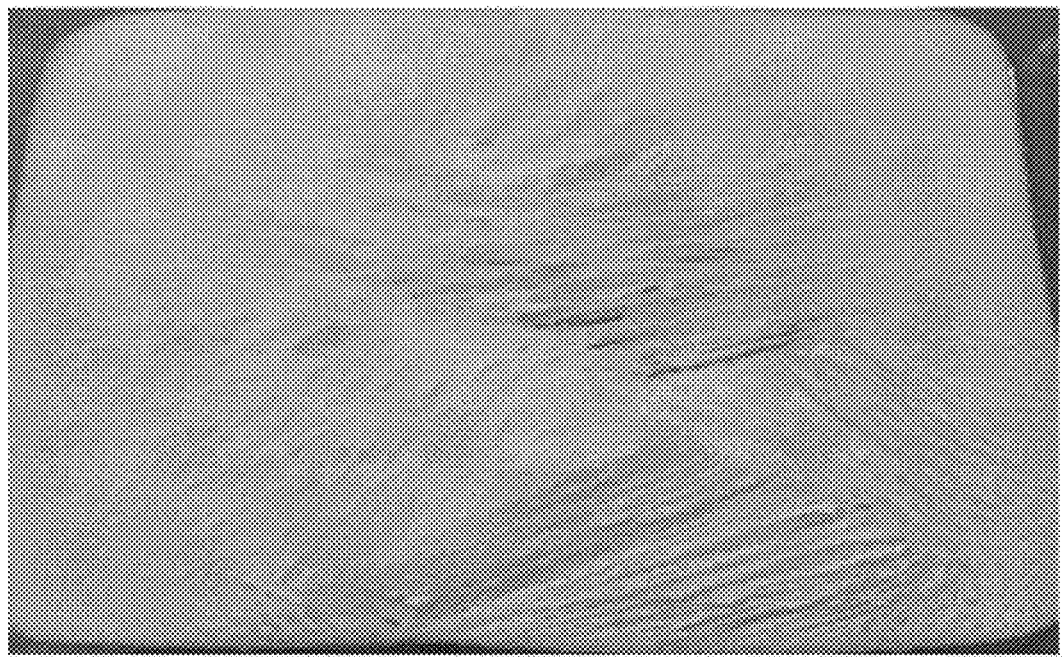

[Fig. 9]
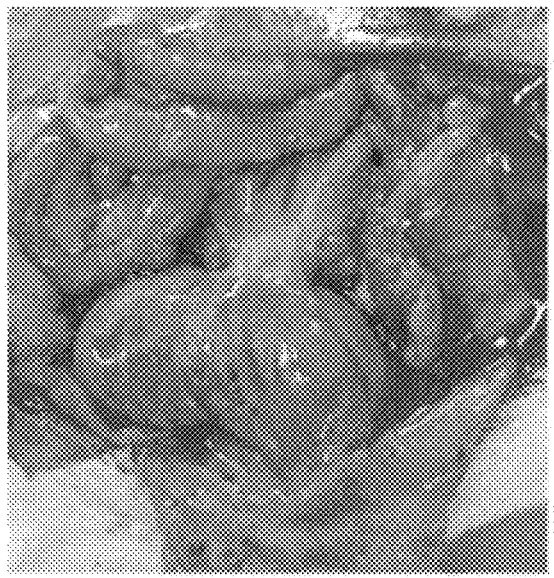 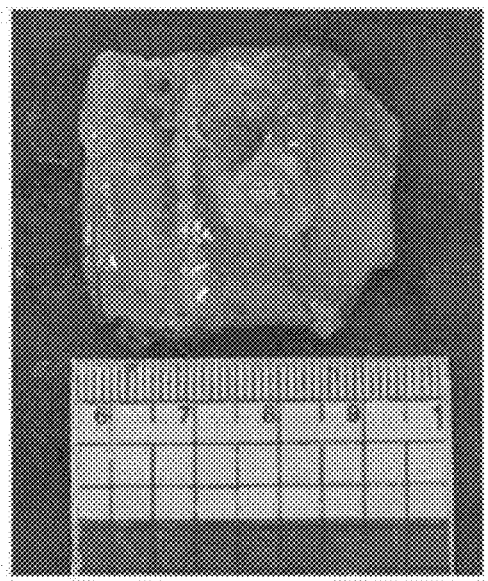
[Fig. 10]
 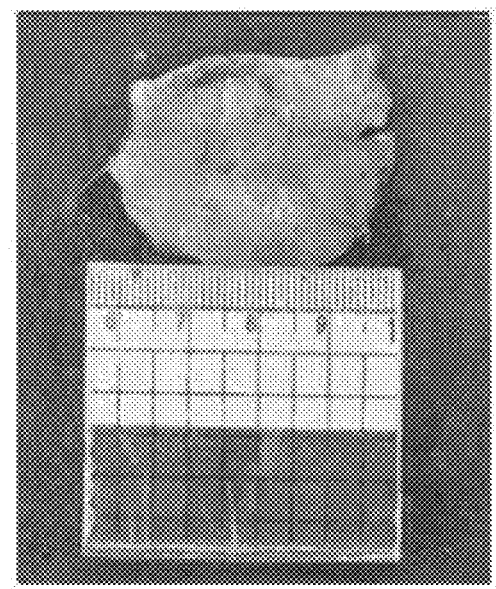

[Fig. 11]
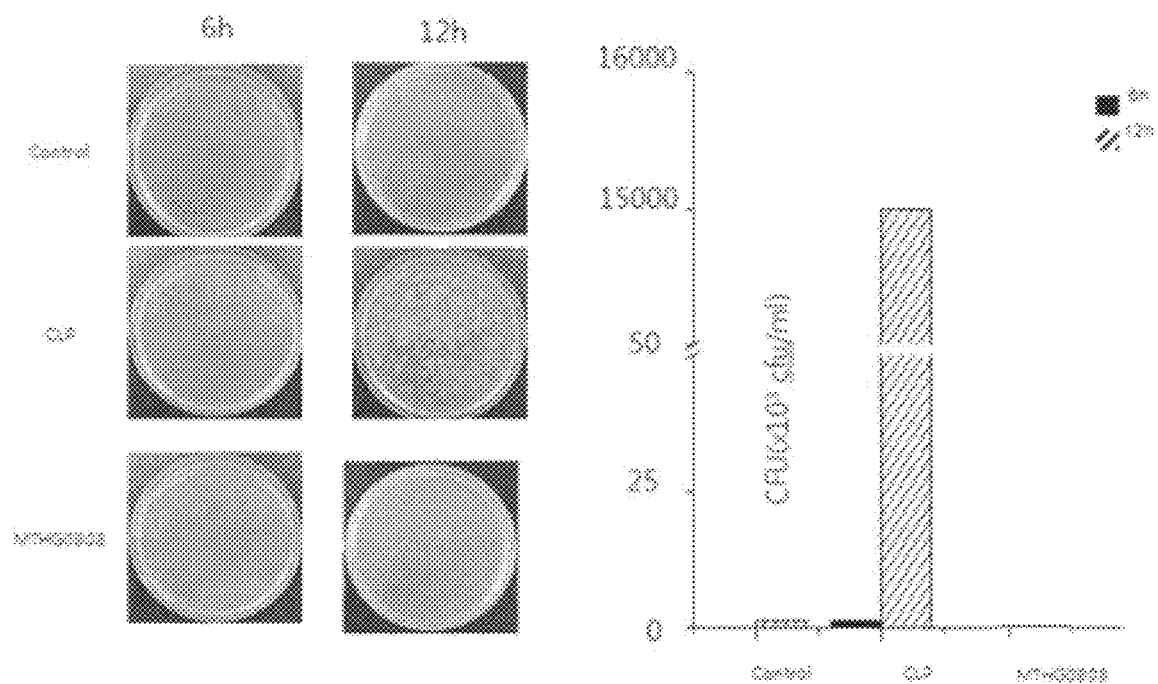

METHOD FOR PREPARING WOUND DRESSING MATERIAL USING BIOPOLYMER AND WOUND DRESSING MATERIAL USING BIOPOLYMER PREPARED THEREBY

CROSS-REFERENCE TO RELATED APPLICATIONS

This application is a U.S. national stage entry under 35 U.S.C. § 371 of PCT International Patent Application No. PCT/KR2016/000693, filed Jan. 22, 2016, which claims benefit of Korean Patent Application No. 10-2015-0015042, filed Jan. 30, 2015 and Korean Patent Application No. 10-2016-0006839, filed Jan. 20, 2016, the contents of each of which are incorporated herein by reference into the subject application.

BACKGROUND OF THE INVENTION

Field of the invention

The present invention relates to a method for preparing a wound dressing material using a biopolymer and a wound dressing material using a biopolymer prepared thereby. The wound dressing material prepared according to the present invention can have excellent effects of inhibiting wound infections and preventing adhesions.

Related Art

A postoperative wound infection is one of the most common nosocomial infections, accounting for 38% of infections in all the infected patients. Based on the U.S. Center for Disease Control and Preservation (CDC) National Nosocomial Infection Surveillance (NNIS) system reports, surgical site infections (SSIs) are the third most common nosocomial infection, accounting for 14% to 16% of all nosocomial infections among hospitalized patients. Another report shows that about 27 million annual surgical procedures are performed and 675,000 SSIs occur in the US, and 30 million annual surgical procedures are performed and 900,000 SSIs occur in Europe. The SSIs act as a negative factor on the postoperative morbidity and recovery period, causing serious problems in patients, operators, and overall health care industries, resulting in an increased hospital length of stay and an increased medical insurance budget. Many countries have significantly reduced the SSI outbreak rate due to the development of surgical techniques and aseptic techniques over the years, but such progress has caused other problems, such as increasing resistant strains and increasing high-risk surgical patients. Especially, the risk of SSI was shown to increase in the surgery of patients with diabetes or obese, and the morbidity rate in this field is also a major concern for related workers. The World Health Organization expects that the number of diabetic patients to reach 300 million from 171 million in the year of 2010, and thus special attention is needed for SSI.

Among the endeavors to prevent SSI, in addition to strict aseptic environment and the application of surgery technique on the basis thereof, the use of antibiotics may be considered in view of the prevention. However, a direct intravascular administration of antibiotics for a long period of time may cause antibiotic resistance and the resultant toxicity risk, and thus a cautious approach is needed for the application of antibiotics. The appearance of products (Gentacoll® and Collatemp G®) for the local use, such as absorbable gentamicin-collagen implants (GCI), disclosed in U.S. Pat. No. 1,321,818 and US 2014/0038915 A1, may be helpful in solving such problems.

Rather than a direction injection, a local use of gentamicin may be performed at a significantly high concentration on the wound site, and on the contrary, gentamicin may be present at a relatively low concentration in the blood, and thus may reduce the risk of side effects or toxicity compared with the above-mentioned intravascular injection. In addition, these methods can anticipate an avoidance of the resistance problem caused by the administration of low concentrations of antibiotics for a long period of time, and an action of high-concentration gentamicin as a broad spectrum of antibiotic. Actually, it was verified that the gentamicin-resistant strains were killed with high-concentration local treatment, and it was reported that these products, which were used for the preventive or therapeutic purpose, reduced the risk of SSI in the surgical operations in several fields (cardiovascular and orthopedic surgery).

In addition, a postoperative adhesion refers to adhering of adjacent organs or tissues to each other, which need to be separated from each other, caused by fibrous tissues, which are excessively generated, and the blood, which flows out and coagulates, in the healing procedure of wounds, such as wounds from inflammations, wounds, friction, or surgery, and thus the postoperative adhesion may occur after all kinds of surgeries. Due to this, the organs or tissues around the operated site adhere to each other, causing serious clinical sequelae.

Generally, the incidence of postoperative organ adhesions is reportedly in a range of 55% to 93% (Ann. Royal Coll. Surg. Engl., 75, 147-153, 1993). A large percentage of abdominal surgeries result in adhesions. Although some of these adhesions may undergo spontaneous decomposition, but in most cases, the adhesion exists even after wound healing, causing a variety of sequelae. There are a variety of kinds of sequelae. The US statistical data show that postoperative adhesions entail, as main symptoms, 49% to 74% of enterocleisis, 15% to 20% of infertility, 20% to 50% of chronic pelvic pain, and about 19% of enterobrosia in a subsequent surgery (Eur. J. Surg., Suppl 577, 32-39, 1997).

The mechanism of intraperitoneal adhesion formation is specifically described in the paper published by Granger (Infert. Reprod. Med. Clin. North Am., 5:3, 391-404, 1994). According to Granger, adhesions are initiated by fibrin resulting from the clotting process of blood among exudates generated after surgeries. The inflammatory exudate is rich in fibrin which forms a clot of blood on wound surfaces. As fibrin is decomposed, mesothelium is regenerated, which normally results in wound healing. The decomposition of fibrin is dependent on the conversion of plasminogen into plasmin, which is a fibrinolytic enzyme, and this reaction is promoted by a tissue plasminogen activator (tPA) existing in the mesothelium and the underlying stroma. However, if the decomposition of fibrin does not occur, inflammatory cells and fibroblasts infiltrate into the fibrin matrix to result in organized adhesions. As described above, adhesions take place through a series of the fibrinogenesis mechanism and the fibrinolysis mechanism, and the relationship therebetween is not simple and is closely related to the healing process of wounds.

As one of various methods for preventing such adhesions, intensive research has been focused on an anti-adhesion agent that prevents the formation of adhesions between adjacent tissues, through the formation of a physical barrier during healing of wounds of tissues using a barrier, as similarly in the action of a surfactant. The anti-adhesion agents used for these barriers may be largely divided into two classes according to the morphology: one is a membrane type barrier including a film type, a non-woven type, and a sponge type, and the other is a solution type barrier including a gel type.

Examples of the membrane type anti-adhesion material include oxidized-regenerated cellulose, expanded polytetrafluoroethylene (hereinafter, referred to as "ePTFE"), films composed of modified hyaluronic acid, sodium carboxymethyl cellulose, and a chemical cross-linking agent, and the like. Examples of the solution type anti-adhesion material include a lactated Ringer's solution, a dextran-70 solution, a heparin solution, a sodium carboxymethyl cellulose solution, a hyaluronic acid solution, a chondroitin sulfate solution, a polyethylene glycol solution, a poloxamer solution, and the like. Among these solution type anti-adhesion materials, the lactated Ringer's solution, dextran-70 solution, heparin solution, and the like, have a main mechanism in which, during healing of the peritoneum, the fibrin-covered surfaces are floated each other. Although the materials are preparations which have been used to inhibit adhesions by separating tissues from each other, satisfactory anti-adhesion effects are not obtained due to their rapid absorption into the peritoneum (Am. Surg., 63, 775-777, 1983). Since polyethylene glycol and the like are not decomposed in vivo, only a low-molecular weight material, which can be discharged through a metabolic pathway at the time of absorption, may be used. However, the use of such a low-molecular weight material results in excessively rapid absorption, so that it cannot serve as an effective barrier to prevent adhesions for an extended period of time.

Meanwhile, hyaluronic acid disclosed in U.S. Pat. No. 4,141,973 is a linear macromolecular polysaccharide composed of alternately bonded β-D-N-acetylglucosamine and β-D-glucuronic acid, and is known to exhibit excellent biocompatibility even when it is transplanted or infused in vivo. However, also due to in vivo decomposition and absorption within a relatively short period of time, there is a limitation in terms of performance as an anti-adhesion agent. As an attempt to improve such disadvantages, U.S. Pat. No. 6,387,413 B1 discloses a hyaluronic acid gel composition prepared by adding a polymer compound, such as carboxymethyl cellulose, for the purpose of supplementing physical properties of hyaluronic acid gel per se. Although the materials that have developed until now show potentialities for the prevention of adhesions, since the chemical cross-linking method is mainly employed, there are problems associated with inconveniences of removing cross-linking agents or additives, complicated processes, and toxicity and safety.

Meanwhile, collagen is one of the most abundant proteins on the earth, and can be extracted from almost all biological organisms. The collagen mainly used in the tissue engineering is extracted from the bovine skin or muscle or porcine skin. However, collagen itself is a protein involved in the immune response, and the collagen, of which the immune response is minimized through the removal of telopeptide, also has a helical structure, but the amino acid sequence or the like on the collagen surface is reported to cause an immune response, and moreover, the scientific base that bovine-derived collagen has complete safety against bovine spongiform encephalopathy (BSE) factor is not sufficient.

SUMMARY OF THE INVENTION

The present inventors have endeavored to develop a material which can substitute for a high-priced collagen material playing a role as a support in the gentamicin-collagen implant and to develop a multi-functional material which achieves purposes of recovering postoperative wounds and preventing adhesions, and as a results, the present inventors have found that a wound dressing material with a soft texture and a uniform surface, having effects of inhibiting wound infections and preventing adhesions, can be prepared by using a biopolymer based on hyaluronic acid.

In a first aspect, a method for preparing a dressing material for inhibiting wound infections and preventing adhesions is provided. The method includes:
preparing a solution using an antibiotic and hyaluronic acid or a salt thereof;
freezing the prepared solution under rotation; and
drying the frozen solution.

In a second aspect, a method for preparing a dressing material for inhibiting wound infections and preventing adhesions is provided. The method includes:
i) preparing a solution using an antibiotic and hyaluronic acid or a salt thereof;
ii) freezing the prepared solution;
iii) thawing the frozen solution;
iv) refreezing the thawed solution; and
v) drying the re-frozen solution. In the aspect, steps ii) to iii) may be repeated two to six times.

In a third aspect, a method for preparing a dressing material for inhibiting wound infections and preventing adhesions is provided. The method includes:
i) preparing a solution using an antibiotic and hyaluronic acid or a salt thereof;
ii) leaving the prepared solution at a low temperature for 8 hours;
iii) freezing the solution left at a low temperature; and
iv) drying the frozen solution. In the aspect, the low temperature may be 0-10° C.

The hyaluronic acid wound dressing material prepared by the method according to the present invention has a soft texture and a uniform surface, and thus can substitute for collagen. Furthermore, the hyaluronic acid wound dressing material prepared by the method according to the present invention has excellent effects of inhibiting wound infections and preventing adhesions.

BRIEF DESCRIPTION OF THE DRAWINGS

FIG. 1 shows an image of a wound dressing material prepared according to example 1.

FIG. 2 shows a wound dressing material prepared according to example 2.

FIG. 3 shows a wound dressing material prepared according to example 3.

FIG. 4 shows a wound dressing material prepared according to example 4.

FIG. 5 shows a wound dressing material prepared according to example 5.

FIGS. 6 and 7 show wound dressing materials prepared according to comparative example 1.

FIG. 8 shows a wound dressing material prepared according to comparative example 2.

FIG. 9 shows images of an adhesion in a rat administered with a control according to test example 1.

FIG. 10 shows images of an adhesion in a rat administered with example 5 according to test example 1.

FIG. 11 shows infection inhibition test results in an enteric infection model according to test example 2.

DESCRIPTION OF EXEMPLARY EMBODIMENTS

The terminologies used herein are not intended to limit the present invention but to describe specific embodiments.

A singular expression may include a plural expression unless it clearly expresses different meaning in context. It shall be noted that in the present application, the terms such as "include" and "have" are intended to indicate that a feature, a figure, a step, an operation, a configuration element, a part, or a combination thereof may exist but are not intended to exclude in advance the possibility of existence or addition of one or more other features, figures, steps, operations, configuration elements, parts, or combinations thereof.

Unless defined otherwise, all the terminologies used herein including technical or scientific terminologies have the same meaning as those understood by a person having an ordinary skill in the art to which the present invention belongs. Terminologies as defined in a generally used dictionary should be interpreted to have the same meaning as those of the terminologies in context in the related descriptions, and shall not be interpreted in an ideal or excessively formal meaning unless they are explicitly defined herein.

The present invention is to provide a method for preparing a wound dressing material using hyaluronic acid as a biopolymer and a wound dressing material prepared by the method.

As used herein, the term "hyaluronic acid" refers to a linear polymer that contains N-acetyl glucosamine and glucuronic acid as basic units, has a molecular weight of several millions, retains the same structure in almost all biological organisms, and is a component of the extracellular matrix. Since the hyaluronic acid has the same structure in different species, it is known to be a polymer without an immune response regardless of sources of extraction thereof. The hyaluronic acid is, until now, a safe natural polysaccharide that is used in many fields, such as degenerative arthritis, cataracts, wrinkles improvement, drug delivery, scaffold of stem cells, moisture-retaining ingredients of cosmetics, and the like.

The hyaluronic acid was extracted from livestock, such as cow and chicken, but is currently produced by microorganism fermentation. Therefore, such hyaluronic acid is safe against factors harmful to the human body, such as bovine spongiform encephalopathy or avian influenza, and can substitute for a relatively high priced collagen.

However, when the hyaluronic acid is used to manufacture products, such as general pads, patches, and sheets, the manufactured products are crispy and fragile after the freeze-drying process, and during the freezing procedure, the grain may be generated in the product, or a dried product with a coarse surface may be produced, and therefore, it is impossible to prepare the same texture as in existing collagen products.

According to an embodiment, provided is a method for preparing a dressing material for inhibiting wound infections and preventing adhesions, the method including:
preparing a solution using an antibiotic and hyaluronic acid or a salt thereof;
freezing the prepared solution under rotation; and
drying the frozen solution.

In the embodiment, the antibiotic may be at least one selected from the group consisting of cephalosporin-based, β-lactam-based, aminoglycoside-based, macrolide-based, quinolone-based, and tetracycline-based antibiotics, but is not limited thereto.

In the embodiment, the salt of hyaluronic acid may be at least one selected from the group consisting of sodium hyaluronate, potassium hyaluronate, calcium hyaluronate, magnesium hyaluronate, zinc hyaluronate, cobalt hyaluronate, and tetrabutyl ammonium hyaluronate, but is not limited thereto.

In the embodiment, the molecular weight of the hyaluronic acid may be 10,000-3,000,000 Da.

In the embodiment, the concentration of the hyaluronic acid may be 0.1-5% (w/v).

In the embodiment, the concentration ratio of the antibiotic and the hyaluronic acid may be 2:1 to 1:10.

In the embodiment, the solution may have a pH of 4.0-8.0.

According to another embodiment, provided is a method for preparing a dressing material for inhibiting wound infections and preventing adhesions, the method including:
i) preparing a solution using an antibiotic and hyaluronic acid or a salt thereof;
ii) freezing the prepared solution;
iii) thawing the frozen solution;
iv) refreezing the thawed solution; and
v) drying the re-frozen solution. In the embodiment, steps i) to ii) may be repeated two to six times.

In the embodiment, the antibiotic may be at least one selected from the group consisting of cephalosporin-based, β-lactam-based, aminoglycoside-based, macrolide-based, quinolone-based, and tetracycline-based antibiotics, but is not limited thereto.

In the embodiment, the salt of hyaluronic acid may be at least one selected from the group consisting of sodium hyaluronate, potassium hyaluronate, calcium hyaluronate, magnesium hyaluronate, zinc hyaluronate, cobalt hyaluronate, and tetrabutyl ammonium hyaluronate, but is not limited thereto.

In the embodiment, the molecular weight of the hyaluronic acid may be 10,000-3,000,000 Da.

In the embodiment, the concentration of the hyaluronic acid may be 0.1-5% (w/v).

In the embodiment, the concentration ratio of the antibiotic and the hyaluronic acid may be 2:1 to 1:10.

In the embodiment, the solution may have a pH of 4.0-8.0.

According to still another embodiment, provided is a method for preparing a dressing material for inhibiting wound infections and preventing adhesions, the method including:
i) preparing a solution using an antibiotic and hyaluronic acid or a salt thereof;
ii) leaving the prepared solution at a low temperature for 8 hours;
iii) freezing the solution left at a low temperature; and
iv) drying the frozen solution. The low temperature may be 0-10° C.

In the embodiment, the antibiotic may be at least one selected from the group consisting of cephalosporin-based, β-lactam-based, aminoglycoside-based, macrolide-based, quinolone-based, and tetracycline-based antibiotics, but is not limited thereto.

In the embodiment, the salt of hyaluronic acid may be at least one selected from the group consisting of sodium hyaluronate, potassium hyaluronate, calcium hyaluronate, magnesium hyaluronate, zinc hyaluronate, cobalt hyaluronate, and tetrabutyl ammonium hyaluronate, but is not limited thereto.

In the embodiment, the molecular weight of the hyaluronic acid may be 10,000-3,000,000 Da.

In the embodiment, the concentration of the hyaluronic acid may be 0.1-5% (w/v).

In the embodiment, the concentration ratio of the antibiotic and the hyaluronic acid may be 2:1 to 1:10.

In the embodiment, the solution may have a pH of 4.0-8.0.

The hyaluronic acid wound dressing material prepared by the method according to the present invention has a soft texture and a uniform surface, and thus can be expected to substitute for collagen.

Hereinafter, the present invention will be described in detail with reference to examples. These examples are only for illustrating the present invention more specifically, and it will be apparent to those skilled in the art that the scope of the present invention is not limited by these examples.

EXAMPLE

Example 1

Preparation of Gentamicin-Containing Hyaluronic Acid Wound Dressing Material (Rotary Freezing)

0.6% gentamicin and 0.9% NaCl were dissolved in a 0.3% (w/v) sodium hyaluronate solution, and adjusted to pH 6.5 with a thin NaOH solution. Then, the solution was put in a cylindrical flask, immersed in a bath of −20° C., and then frozen with rotation at 100 rpm. After the freezing was completed, the frozen material was dried using a freeze-dryer for 72 hours (FIG. 1). As a result, as shown in FIG. 1, a wound dressing material with a soft and smooth surface was obtained.

Example 2

Preparation of Gentamicin-Containing Hyaluronic Acid Wound Dressing Material (Rotary Freezing)

A gentamicin-containing hyaluronic acid wound dressing material was prepared by the same method as in example 1 except that 0.5% (w/v) of sodium hyaluronate was added (FIG. 2). As a result, as shown in FIG. 2, a wound dressing material with a soft and smooth surface was obtained.

Example 3

Preparation of Gentamicin-Containing Hyaluronic Acid Wound Dressing Material (Rotary Freezing)

A gentamicin-containing hyaluronic acid wound dressing material was prepared by the same method as in example 1 except that 0.8% (w/v) of sodium hyaluronate was added (FIG. 3). As a result, as shown in FIG. 3, a wound dressing material with a soft and smooth surface was obtained.

Example 4

Preparation of Gentamicin-Containing Hyaluronic Acid Wound Dressing Material (Freezing/Thawing)

0.6% gentamicin and 0.9% NaCl were dissolved in a 0.8% (w/v) sodium hyaluronate solution, and adjusted to pH 6.5 with a thin NaOH solution. Then, 50 ml of the solution was put in a square petri dish, primarily frozen at −20° C. for 5 hours, and then left to be thawed at room temperature. After the thawing was completed, the thawed material was secondarily frozen for 5 hours under the same temperature condition as in the primary freezing, and then dried in a freeze-dryer for 72 hours (FIG. 4). As a result, as shown in FIG. 4, a wound dressing material with a soft and smooth surface was obtained.

Example 5

Preparation of Gentamicin-Containing Hyaluronic Acid Wound Dressing Material (Being Left at Low Temperature)

0.6% gentamicin and 0.9% NaCl were dissolved in a 1.0% (w/v) sodium hyaluronate solution, and adjusted to pH 6.5. Next, 50 ml of the solution was put in a petri dish, left in a place at 10° C. for 8 hours, frozen at −20° C., and then dried in a freeze-dryer for 72 hours (FIG. 5). As a result, as shown in FIG. 5, a wound dressing material with a soft and smooth surface was obtained.

Comparative Example 1

Preparation of Gentamicin-Containing Hyaluronic Acid Wound Dressing Material (Normal Method)

0.6% gentamicin and 0.9% NaCl were dissolved in a 0.8% (w/v) sodium hyaluronate solution, and adjusted to pH 6.5 with a thin NaOH solution. 50 ml of the solution was put in a square petri dish, frozen at −20° C. for 5 hours, and then dried in a freeze-dryer for 72 hours (FIG. 7).

As can be seen from FIGS. 6 and 7, the grain was generated or a non-uniform surface was formed in the frozen solution, and thus, the dried material was fragile at the time of use, or the dried material was difficult to apply to a wound site.

Comparative Example 2

Preparation of Gentamicin-Containing Hyaluronic Acid Wound Dressing Material II 0.6% Gentamicin and 0.9% NaCl were dissolved in 0.8% (w/v) sodium hyaluronate, and 50 ml of the solution, without pH adjustment, was put in a square petri dish, and then primarily frozen at −20° C. for 5 hours, and the petri dish was left to be thawed at room temperature. Next, after the thawing was completed, the thawed material was secondarily frozen for 5 hours under the same temperature condition as in the primary freezing, and then dried in a freeze-dryer for 72 hours (FIG. 8). As a result, as can be seen from FIG. 8, the wound dressing material had a non-uniform surface and was fragile.

TEST EXAMPLE

Test Example 1

Anti-Adhesion Test in Rat Cecum/Abdominal Wall Abrasion Model

In order to evaluate the anti-adhesion performance of the wound dressing materials prepared in the above examples, a rat cecum/abdominal wall abrasion model was used. As experimental animals, 7-week old male Sparague-Dawley rats (SLC, Japan) were used, and five animals were used per group. For induction of adhesions, the experimental animals were anesthetized by peritoneal administration of Ketamin·KCL (0.1 ml/100 g), followed by abdominal shaving and disinfection with 70% ethanol, and a 4-5 cm incision was then made on the midline at abdominal region. Thereafter, the cecum was taken out, and a damage (1.2 cm×1.2 cm) was applied to the serous membrane using sterilized gauze such that hemorrhage occurred, and a damage with the same size was applied to the opposite peritoneal membrane using a reagent spoon. Two spots, which were 1 cm away from the rubbing-injured regions, were fixed by a 5-0 nylon suture such that two damaged surfaces were touched each other, thereby promoting the formation of adhesions.

A negative control group was infused with physiological saline. For experimental groups, each of the dressing materials prepared in examples 1 to 5 and comparative examples 1 and 2 was cut into 1 cm×1 cm, and the cut dressing material was attached to the damaged site. Then, the peritoneal membrane and skin were sutured. After surgeries were completed, the animals were grown for one week while being fed with a sufficient diet and water, and then were sacrificed. Using an adhesion evaluation system, scores obtained were summed up and averaged (Am. J. Obstet. Gynecol., 146, 88-92, 1983), and the results were tabulated in Table 1.

The adhesion extent was evaluated according to the following criteria on a scale of 0 to 5 (0: No adhesions, 1: One thin film-like adhesion, 2: Two or more thin film-like adhesions, 3: Focal localized thick adhesions, 4: Plate-like localized adhesions, 5: Very thick adhesions with formation of blood vessels or one or more plate-like dense adhesions).

The adhesion strength was evaluated according to the following criteria on a scale of 1 to 4 (1: film-like adhesion which is easily releasable by very weak force, 2: adhesion which requires moderate force to release the adhesion, 3: Adhesion which is releasable with application of considerable pressure, 4: Very strong adhesion difficult to release or requiring very high pressure to release the adhesion).

TABLE 1

|  | Adhesion extent | Adhesion strength | Adhesion area (cm$^2$) | Reduciton rate of adhesion area (%) |
| --- | --- | --- | --- | --- |
| Control | 3.73 ± 0.46 | 3.00 ± 0.00 | 0.80 ± 0.16 | 0 |
| Example 1 | 1.75 ± 1.07** | 1.35 ± 0.84** | 0.16 ± 0.08** | 80.0 |
| Example 2 | 1.65 ± 1.15** | 1.30 ± 0.76** | 0.12 ± 0.08** | 85.0 |
| Example 3 | 1.50 ± 1.08** | 1.25 ± 0.84** | 0.12 ± 0.12** | 85.0 |
| Example 4 | 1.40 ± 1.26** | 1.20 ± 0.84** | 0.07 ± 0.11** | 91.1 |
| Example 5 | 1.20 ± 1.30** | 0.80 ± 0.84** | 0.06 ± 0.10** | 92.5 |
| Comparative Example 1 | 1.75 ± 1.26* | 1.25 ± 0.96** | 0.26 ± 0.09** | 67.5 |
| Comparative Example 2 | 2.25 ± 0.50 | 1.50 ± 1.00* | 0.27 ± 0.18** | 62.5 |

Data were represented by mean ± S.D(n = 5).
*p < 0.05 versus None (negative control),
**p < 0.05 versus None (negative control)

As shown in Table 1 above, the groups administered with examples 1 to 5 prepared by the preparing method according to the present invention exhibited a significant reduction in tissue adhesions, compared with the control group. These results can be confirmed through FIGS. 9 and 10 showing adhesion result images according to the control group and example 5.

Meanwhile, the groups administered with comparative examples 1 and 2 prepared by the conventional preparing method exhibited a slight reduction in adhesion, compared with the control group, but showed a significantly low rate of adhesion compared with the groups administered with examples 1 to 5, due to non-uniform texture of the dressing material.

Test Example 2

Infection Inhibition Test in Enteric Infection Model

In order to evaluate the infection inhibition performance of the wound dressing material prepared in example 5 above, the enteric infection model was used in Balb/C male mice. Infection inhibition test groups were classified into a control test group, a CLP test group, and a group administered with a wound dressing material prepared in example 5. Ten male Balb/c mice were used for each group (6 mice for the control test group), and the wound dressing material was cut into 1×1 cm$^2$, which was then inserted. Specifically, on the day before the test, the mouse abdomen was shaved, and the next day, the mouse was anesthetized by peritoneal administration of an anesthetic agent, Avertin (300 mg/kg), for 20 minutes. The abdomen of the mouse was disinfected three times with povidone and 70% ethanol alternatively. In addition, a 2-3 cm incision was made at the region, which was 1 cm away left from the midline at abdomen, and the cecum was taken out. A region of the cecum, which was ¾ distanced from the bottom, was tied with a black silk, and then a hole is formed by punching the cecum using a 21 G syringe needle, through which a small amount of contents were then squeezed from the cecum. For the CLP test group, the cecum was again put in the abdomen, followed by suturing. For the group administered with the wound dressing material prepared in example 5, the cecum was again put in the abdomen, and then a wound dressing material (1×1 cm$^2$) was put in the abdomen, followed by suturing. The number of infectious bacteria was determined by taking out the seroperitoneum from the mouse 6 and 12 hours after surgery, culturing the seroperitoneum on the LB plate, and measuring the number of colonies after about 18 hours. The results were shown FIG. 11.

As shown in FIG. 11, when the seroperitoneum taken-out 6 hours after surgery was cultured, the colonies were not generated in the group administered with the wound dressing material of example 5, prepared by the method according to the present invention, but the colonies were measured to be 1.5×10$^3$ cfu/ml in the CLP test group. For the seroperitoneum 12 hours after surgery, the colonies were measured to be 1.5×10$^3$ cfu/ml and 1.5×10$^2$ cfu/ml in the control test group and the CLP test group, respectively, but the colonies were not generated in the group administered with the wound dressing material of example 5, prepared by the method according to the present invention.

The descriptions of particular structures and functions are exemplified for the purpose of illustrating the examples of the present invention. The embodiment of the present invention may be implemented in various forms, and should be intended to cover all the modifications, equivalents, and substitutions belonging to the technical idea and technical scope of the present invention.

What is claimed is:

1. A method for preparing a dressing material with a uniform surface, the method comprising:
    i) preparing an aqueous solution using gentamicin and 0.1-5% (w/v) sodium hyaluronate in the range of pH of 6.5;
    ii) leaving the prepared aqueous solution at 10° C. for 8 hours;
    iii) freezing the aqueous solution at −20° C.; and
    iv) drying the frozen aqueous solution in a freeze-dryer for 72 hours, thereby preparing a dressing material with a uniform surface which inhibits wound infections and adhesions.

2. The method of claim 1, wherein the molecular weight of the hyaluronic acid is 10,000 to 3,000,000 Da.

\* \* \* \* \*